US009448296B2

United States Patent
Wang et al.

(10) Patent No.: US 9,448,296 B2
(45) Date of Patent: Sep. 20, 2016

(54) MOTION-SENSITIZED DRIVEN EQUILIBRIUM BLOOD-SUPPRESSION SEQUENCE FOR VESSEL WALL IMAGING

(75) Inventors: Jinnan Wang, Seattle, WA (US); Vasily Yarnykh, Seattle, WA (US); Chun Yuan, Bellevue, WA (US)

(73) Assignee: University of Washington, Seattle, WA (US)

( * ) Notice: Subject to any disclaimer, the term of this patent is extended or adjusted under 35 U.S.C. 154(b) by 1582 days.

(21) Appl. No.: 12/922,257

(22) PCT Filed: Feb. 20, 2009

(86) PCT No.: PCT/US2009/034686
§ 371 (c)(1),
(2), (4) Date: Dec. 14, 2010

(87) PCT Pub. No.: WO2009/117211
PCT Pub. Date: Sep. 24, 2009

(65) Prior Publication Data
US 2011/0092797 A1    Apr. 21, 2011

Related U.S. Application Data

(60) Provisional application No. 61/037,644, filed on Mar. 18, 2008.

(51) Int. Cl.
*A61B 5/05* (2006.01)
*G01R 33/56* (2006.01)
(Continued)

(52) U.S. Cl.
CPC ............... *G01R 33/56* (2013.01); *A61B 5/05* (2013.01); *G01R 33/5617* (2013.01); *G01R 33/563* (2013.01); *G01R 33/5607* (2013.01)

(58) Field of Classification Search
None
See application file for complete search history.

(56) References Cited

U.S. PATENT DOCUMENTS

| 5,050,609 A | 9/1991 | Balaban et al. ........ 128/653 CA |
| 5,051,698 A | 9/1991 | Ordidge ........................ 324/309 |

(Continued)

OTHER PUBLICATIONS

Wang et al. ("Improved Suppression of Plaque-Mimicking Artifacts in Black-Blood Carotid Atherosclerosis Imaging Using a Multislice Motion-Sensitized Driven-Equilibrium (MSDE) Turbo Spin-Echo (TSE) Sequence", Magnetic Resonance in Medicine 58:973-981, 2007).*

(Continued)

*Primary Examiner* — Amanda Lauritzen Moher
*Assistant Examiner* — Shahdeep Mohammed
(74) *Attorney, Agent, or Firm* — Kilpatrick Townsend and Stockton LLP

(57) ABSTRACT

An improved motion-sensitization driven equilibrium (iMSDE) sequence based upon an MLEV-4 sequence is used for black-blood vessel wall imaging. The MSDE pulse pattern that is used us a preparation sequence for other procedures employed to acquire images has been modified to produce the iMSDE sequence by the addition of a second 180 degree refocusing pulse and two motion sensitization gradients. The iMSDE sequence thus includes a group of four radio frequency (RF) pulses, as well as additional magnetic gradient pulses that are not included in the conventional MSDE sequence. Computer simulations indicate that this new pulse sequence is substantially more immune to local B1 inhomogeneity than conventional sequences. In vivo experiments have demonstrated significant signal improvement at high first-order moments ($m_1$) conditions compared to the traditional MSDE sequence.

34 Claims, 5 Drawing Sheets

(51) Int. Cl.
G01R 33/561 (2006.01)
G01R 33/563 (2006.01)

(56) References Cited

U.S. PATENT DOCUMENTS

| | | | | |
|---|---|---|---|---|
| 5,256,967 | A | 10/1993 | Foo et al. | 324/311 |
| 5,285,158 | A | 2/1994 | Mistretta et al. | 324/309 |
| 5,588,431 | A | 12/1996 | Mani et al. | 128/653.3 |
| 5,810,728 | A | 9/1998 | Kuhn | 600/410 |
| 5,908,386 | A | 6/1999 | Ugurbil et al. | 600/410 |
| 6,320,377 | B1 | 11/2001 | Miyazaki et al. | 324/306 |
| 6,486,668 | B1 | 11/2002 | Ma | 324/307 |
| 6,493,569 | B2 | 12/2002 | Foo et al. | 600/420 |
| 6,498,946 | B1 | 12/2002 | Foo et al. | 600/410 |
| 6,526,307 | B2 * | 2/2003 | Foo | 600/413 |
| 6,552,542 | B1 | 4/2003 | Overall | 324/309 |
| 6,943,033 | B2 | 9/2005 | Van Zijl et al. | 436/86 |
| 7,412,277 | B1 | 8/2008 | Saranathan et al. | 600/413 |
| 7,498,808 | B2 | 3/2009 | Asano | 324/307 |
| 7,546,155 | B2 | 6/2009 | Foo et al. | 600/410 |
| 7,627,359 | B2 | 12/2009 | Yarnykh et al. | 600/410 |
| 7,672,704 | B2 | 3/2010 | Viglianti et al. | 600/407 |
| 2006/0080044 | A1 | 4/2006 | Ropele | 702/23 |
| 2006/0253015 | A1 * | 11/2006 | Nezafat et al. | 600/410 |
| 2007/0032956 | A1 | 2/2007 | Blanz et al. | 324/303 |
| 2007/0156045 | A1 * | 7/2007 | Mistretta et al. | 600/410 |

OTHER PUBLICATIONS

Jeong et al. ("High-Resolution Diffusion-Weighted 3D MRI, Using Diffusion-Weighted Driven-Equilibrium (DW-DE) and Multishot Segmented 3D-SSFP Without Navigator Echoes"; Magnetic Resonance in Medicine 50:821-829 (2003)).*
Edzes et al. ("Quantitative T2 Imaging of Plant Tissues by Means of Multi-Echo MRI Microscopy"; Magnetic Resonance Imaging, vol. 16, No. 2, pp. 185-196; 1998).*
Koktzoglou et al. ("Submillimeter Isotropic Resolution Carotid Wall MRI with Swallowing Compensation" Imaging Results and Semiautomated wall Morphometry, Journal of Magnetic Resonance Imaging, vol. 25, Issue 4, pp. 815-823, Apr. 2007).*
Bakshi, Rohit., "Magnetic Resonance Imaging Advances in Multiple Sclerosis." *Journal of Neuroimaging* Supplement to vol. 15, No. 4: 5S-9S, 2005.
Bonk et al., "Time-of-Flight MR Angiography With Gd-DTPA Hexamethylene Diamine Co-Polymer Blood Pool Contrast Agent: Comparison of Enhanced MRA and Conventional Angiography for Arterial Stenosis Induced in Rabbits." *Journal of Magnetic Resonance Imaging*, vol. 11: 638-646, 2000.
Cai et al., "Classification of Human Carotid Atherosclerotic Lesions With In Vivo Multicontrast Magnetic Resonance Imaging." *Circulation, Journal of the American Heart Association*: 1368-1373, Sep. 10, 2002.
Chu et al., "Occurrence and Staging of Hemorrhage in the Advanced Carotid Atherosclerotic Plaque: An In-Vivo Multi Contrast High Resolution MRI Study." *Stroke*: 25pp., Oct. 2003.
Fayad et al., "Noninvasive In Vivo Human Coronary Artery Lumen and Wall Imaging Using Black-Blood Magnetic Resonance Imaging." *Circulation, Journal of the American Heart Association*, vol. 102: 506-510, 2000.
Gochberg et al., "Quantitative Magnetization Transfer Imaging via Selective Inversion Recovery with Short Repetition Times." *Magnetic Resonance in Medicine* vol. 57: 437-441, 2007.
Han et al., "A Fast Minimal Path Active Contour Model." *IEEE Transactions on Image Processing*, vol. 10, No. 6: 865-873, Jun. 2001.
Han et al., "A Multi-Scale Method for Automatic Correction of Intensity Non-Uniformity in MR Images." *Journal of Magnetic Resonance Imaging*, vol. 13: 428-436, 2001.
Han et al., "Detecting Objects in Image Sequences Using Rule-Based Control in an Active Contour Model." *IEEE Transaction on Biomedical Engineering*, vol. 50, No. 6: 705-710, Jun. 2003.

Han et al., "Plaque Morphological Quantitation." *Angiography and Plaque Imaging, Advanced Segmentation Techniques*, Chapter 2: 43-76, 2003.
Hatsukami et al., "Visualization of Fibrous Cap Thickness and Rupture in Human Atherosclerotic Carotid Plaque In Vivo With High-Resolution Magnetic Resonance Imaging." *Circulation, Journal of the American Heart Association*: 959-964, Aug. 29, 2000.
Henkelman et al., "Magnetization Transfer in MRI: a review." *NMR in Biomedicine* vol. 14: 57-64, 2001.
Kaneko et al., "Detection of dissection and remodeling of atherosclerotic lesions in rabbits after balloon angioplasty by magnetic-resonance imaging." *Coronary Artery Disease, Diagnostic Methods*, vol. 11 No. 8.: 599-606, 2000.
Kang et al., "Analysis of the Measurement Precision of Arterial Lumen and Wall Areas Using High-Resolution MRI." Measurement Precision of High-Resolution MRI. *Magnetic Resonance in Medicine*, vol. 44: 968-972, 2000.
Kerwin et al., "A Quantitative Vascular Analysis System for Evaluation of Artherosclerotic Lesions by MRI." *Medical Imaging Computing and Computer-Assisted Intervention—MICCAI 2001*, 4th InternationalConference Utrecht, The Netherlands: 9pp., Oct. 2001.
Kerwin et al., "Analysis and Visualization of Atherosclerotic Plaque Composition by MRI." *Angiography and Plaque Imaging, Advanced Segmentation Techniques*, Chapter 3: 77-117, 2003.
Kerwin et al., "Noise and Motion Correction in Dynamic Contrast-Enhanced MRI for Analysis for Atherosclerotic Lesions." *Magnetic Resonance in Medicine*, vol. 47: 1211-1217, 2002.
Kerwin et al., "Quantitative Magnetic Resonance Imaging Analysis of Neovasculature Volume in Carotid Atherosclerotic Plaque." *Circulation, Journal of the American Heart Association*: 851-856, Feb. 18, 2003.
Kholmovski et al., "A Generalized k-Sampling Scheme for 3D Fast Spin Echo." *Journal of Magnetic Resonance Imaging*, vol. 11: 549-558, 2000.
Luo et al., "Accuracy and Uniqueness of Three In Vivo Measurements of Atherosclerotic Carotid Plaque Morphology With Black Blood MRI." *Magnetic Resonance in Medicine*, vol. 50: 75-82, 2003.
Mai et al., "Effect of Respiratory Phases on MR Lung Signal Intensity and Lung Conspicuity Using Segmented Multiple Inversion Recovery Turbo Spin Echo (MIR-TSE)." *Magnetic Resonance in Medicine*, vol. 43: 760-763, 2000.
Miller et al., "Atherosclerotic Plaque Imaging Techniques in Magnetic Resonance Images." *Angiography and Plaque Imaging, Advanced Segmentation Techniques*, Chapter 7: 299-329, 2003.
Mitsumori et al., "In Vivo Accuracy of Multisequence MR Imaging for Identifying Unstable Fibrous Caps in Advanced Human Carotid Plaques." *Journal of Magnetic Resonance Imaging*, vol. 17: 410-420, 2003.
Naghavi et al., "From Vulnerable Plaque to Vulnerable Patient, A Call for New Definitions and Risk Assessment Strategies: Part I." *Circulation, Journal of the American Heart Association*: 1664-1672, Oct. 7, 2003.
Naghavi et al., "From Vulnerable Plaque to Vulnerable Patient, A Call for New Definitions and Risk Assessment Strategies: Part II." *Circulation, Journal of the American Heart Association*: 1772-1778, Oct. 14, 2003.
Parker et al., "Improved Efficiency in Double-Inversion Fast Spin-Echo Imaging." *Magnetic Resonance Medicine* vol. 47: 1017-1021, 2002.
Ropele et al., "Method for Quantitative Imaging of the Macromolecular $^1$H Fraction in Tissues." *Magnetic Resonance in Medicine* vol. 49: 864-871, 2003.
Saam et al., "Differences in Carotid Artery Atherosclerotic Lesion Characteristics from the Index- and Non-Index Side of Symptomatic Patients: A High-Resolution, Multi Contrast Magnetic Resonance Imaging Study." *Stroke*: 19pp., 2003.
Saam et al., "In Vivo Comparison of the Atherosclerotic Lesion Ipsilateral and Contralateral to the Side of Symptomatic Carotid Disease: A High-Resolution, Multi-Contrast Magnetic Resonance Imaging Study." *Stroke*: 25pp., 2003.
Saam et al., "Vascular Imaging." *Encyclopedia of Biomaterials and Biomedical Engineering*: 26pp., Oct. 2003.

(56) References Cited

OTHER PUBLICATIONS

Schwartz et al., "Molecular Markers, Fibrous Cap Rupture, and the Vulnerable Plaque, New Experimental Opportunities." *Circulation, Journal of the American Heart Association*: 471-473, Sep. 14, 2001.

Sled et al. "Quantitative Imaging of Magnetization Transfer Exchange and Relaxation Properties In Vivo Using MRI." *Magnetic Resonance in Medicine* vol. 46: 923-931, 2001.

Song et al., "Highly Efficient Double-Inversion Spiral Technique for Coronary Vessel Wall Imaging." *Proceedings of the 10th Annual Meeting of ISMRM*, Honolulu: 1566, 2002.

Song et al., "Multislice Double Inversion Pulse Sequence for Efficient Black-Blood MRI." *Magnetic Resonance Medicine* vol. 47: 616-620, 2002.

Tozer et al., "Quantitative Magnetization Transfer Mapping of Bound Protons in Multiple Sclerosis." *Magnetic Resonance in Medicine* vol. 50: 83-91, 2003.

Wang et al., "Improved Suppression of Plaque-Mimicking Artifacts in Black-Blood Carotid Atherosclerosis Imaging Using a Multislice Motion-Sensitized Driven-Equilibrium (MSDE) Turbo Spin-Echo (TSE) Sequence." *Magnetic Resonance in Medicine*, vol. 58: 973-978, 2007.

Winn et al., "Detection and Characterization of Atherosclerotic Fibrous Caps with T2-Weighted MR." *AJNR Am J Neuroradiol*, vol. 19: 129-134, 1998.

Xu et al., "Segmentation of Multi-Channel Image with Markov Random Field Based Active Contour Model." *Kluwer Academic Publishers*, The Netherlands: 11pp., 2002.

Yarnykh et al., "Cross-relaxation imaging reveals detailed anatomy of white matter fiber tracts in the human brain." *NeuroImage*: 409-424, 2004.

Yarnykh et al., "High-Resolution Multi-Contrast MRI of the Carotid Artery Wall for Evaluation of Atherosclerotic Plaques." *Current Protocols in Magnetic Resonance Imaging*, Unit A1.4, Intracranial Arterial Disease. Supplement 11: 18pp., 2003.

Yarnykh et al., "Multislice Double Inversion-Recovery Black-Blood Imaging With Simultaneous Slice Reinversion." *Journal of Magnetic Resonance Imaging*, vol. 17: 478-483, 2003.

Yarnykh, Vasily L., "Pulsed Z-Spectroscopic Imaging of Cross-Relaxation Parameters in Tissues for Human MRI: Theory and Clinical Applications." *Magnetic Resonance in Medicine*, vol. 47: 929-939, 2002.

Yarnykh et al., "$T_1$-Insensitive Flow Suppression Using Quadruple Inversion-Recovery." *Magnetic Resonance in Medicine*, vol. 48: 899-905, 2002.

Yuan et al., "Carotid Atherosclerotic Plaque: Noninvasive MR Characterization and Identification of Vulnerable Lesions." *Radiology*, vol. 221, No. 2: 285-299, Nov. 2001.

Yuan et al., "Carotid atherosclerotic wall imaging by MRI." *Neuroimaging Clinics of North America*, vol. 12: 391-401, 2002.

Yuan et al., "Closed Contour Edge Detection of Blood Vessel Lumen and Outer Wall Boundaries in Black-Blood MR Images." *Magnetic Resonance Imaging*, vol. 17, No. 2: 257-266, 1999.

Yuan et al., "Contrast-Enhanced High Resolution MRI for Atherosclerotic Carotid Artery Tissue Characterizartion." *Journal of Magnetic Resonance Imaging*, vol. 15: 62-67, 2002.

Yuan et al., "High-Resolution Magnetic Resonance Imaging of Normal and Atheroscleroctic Human Coronary Arteries Ex Vivo: Discrimination of Plaque Tissue Components." *Journal of Investigative Medicine*, vol. 49, No. 6: 491-499, Nov. 2001.

Yuan et al., "In Vivo Accuracy of Multispectral Magnetic Resonance Imaging for Identifying Lipid-Rich Necrotic Cores and Intraplaqie Hemorrhage in Advanced Human Carotid Plaques." *Circulation, Journal of the American Heart Association*: 2051-2056, Oct. 23, 2001.

Yuan et al, "Identification of Fibrous Cap Rupture With Magnetic Resonance Imaging Is Highly Associated With Recent Transient Ischemic Attack or Stroke." *Circulation, Journal of the American Heart Association*: 181-185, 2002.

Yuan et al., "Measurement of Atherosclerotic Carotid Plaque Size in Vivo Using High Resolution Magnetic Resonance Imaging." *Circulation, Journal of the American Heart Association*: 2666-2671, Dec. 15, 1998.

Yuan et al., "Quantitative Evaluation of Carotid Atherosclerotic Plaques by Magnetic Resonance Imaging." *Current Atherosclerosis Reports 2002*, vol 4: 351-357, 2002.

Zhang et al., "Comparison of carotid vessel wall area measurements using three difference contrast-weighted black blood MR imaging techniques." *Magnetic Resonance Imaging*, vol. 19: 795-802, 2001.

Zhang et al., "Measurement of Carotid Wall Volume and Maximum Area with Contrast-enhanced 3D MR Imaging: Initial Observations." *Radiology*, vol. 228, No. 1: 200-205, Jul. 2003.

Zhao et al., "Effects of Prolonged Intensive Lipid-Lowering Therapy on the Characteristics of Carotid Atherosclerotic Plaques In Vivo by MRI, A Case-Control Study." *Arterioscler Thromb Vasc Biol.*: 1623-1629, Oct. 2001.

\* cited by examiner

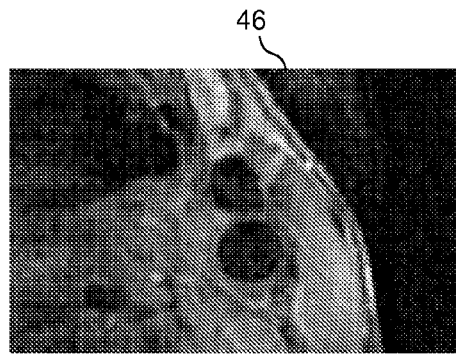
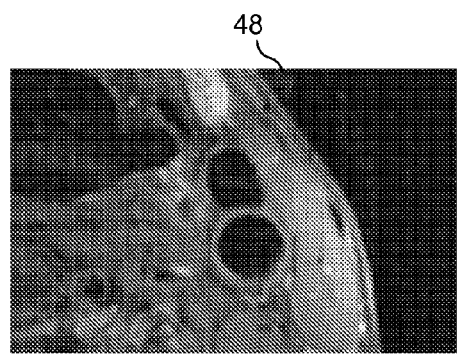
*FIG. 4A*  *FIG. 4B*
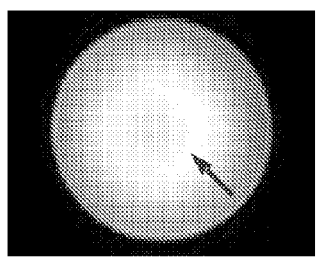
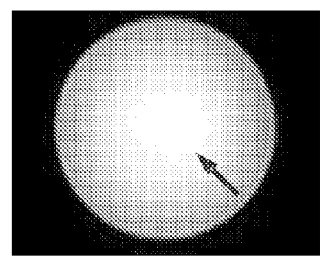
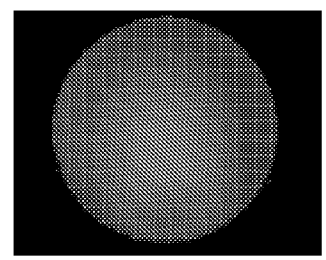
*FIG. 5A*  *FIG. 5B*  *FIG. 5C*
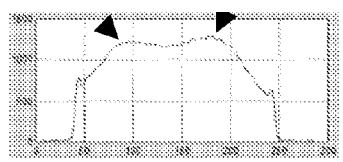
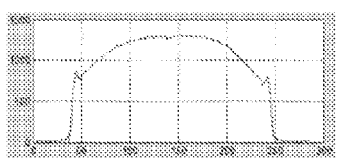
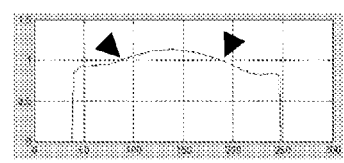
*FIG. 5D*  *FIG. 5E*  *FIG. 5F*
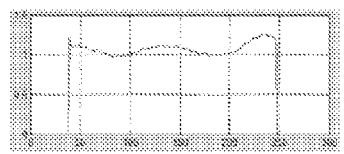
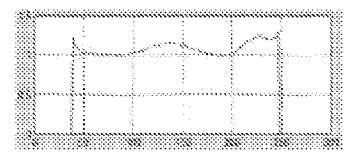
*FIG. 5G*  *FIG. 5H*

ATHEROSCLEROTIC PLAQUE

ATHEROSCLEROTIC PLAQUE

AXIAL VIEW

ATHEROSCLEROTIC PLAQUE

ULCER

SAGITTAL VIEW

CORONAL VIEW

ATHEROSCLEROTIC PLAQUE

MOTION-SENSITIZED DRIVEN EQUILIBRIUM BLOOD-SUPPRESSION SEQUENCE FOR VESSEL WALL IMAGING

RELATED APPLICATIONS

This application is based on a prior provisional application Ser. No. 61/037,644, filed on Mar. 18, 2008, the benefit of the filing date of which is hereby claimed under 35 U.S.C. §119(e).

BACKGROUND

Efficient flowing blood signal suppression is critical for accurate morphology measurements and diagnosis in magnetic resonance (MR) vessel wall imaging. Due to the complicated flow patterns in the carotid artery bifurcation, however, current black-blood (BB) imaging of the carotid bifurcation is frequently compromised by plaque-mimicking artifacts. The currently widely used BB imaging techniques include an in-flow (blood) saturation (IS) technique, and a double inversion recovery (DIR) imaging technique. The IS technique achieves BB imaging by pre-saturating the flowing blood signal before the blood enters the imaging area, and then acquiring images as the signal-suppressed blood flows through the imaging area. The blood suppression capability of the IS technique is primarily limited by the blood replenishing rate, which typically is characterized by a short preparation time.

Because of the relatively short preparation time of the IS technique compared to the DIR technique, the IS technique has been primarily used in fast imaging applications or for other occasions when a long preparation time is unacceptable. Instead of saturating the blood signal as the IS technique does, the DIR technique and its variations achieve BB imaging by inverting the out-of-slice blood signal with a 180 degree pulse and then acquiring images only when the magnetization of inflowing blood has achieved a zero-point, after delaying an appropriate inversion time (TI). The DIR technique works at a lower flow replenishing rate, since it requires the blood to be replaced after a relatively long preparation time (i.e., after a preparation duration corresponding to TI). Because of its better blood suppression capability, the DIR technique is currently widely used in vessel wall imaging applications or on other occasions when better blood suppression is desired. Both IS and DIR techniques, however, are limited by the blood replenishing rate in the through-plane direction and therefore, are both unable to avoid plaque-mimicking artifacts when recirculation occurs, or slow or stagnant flow exists.

Three-dimensional (3-D) image acquisition is of increasing interest in the black-blood imaging area due to the fact that it can provide isotropic voxel size and consequently, can facilitate the image reformation at different orientations. However, conventional imaging techniques that are typically employed for suppressing the effect of flowing blood are not well-suited for use in 3-D images. The traditional black-blood imaging techniques (IS and DIR) are based on the blood replenishing rate for a limited imaging volume. However, insufficient blood suppression will be observed in regions where there is stagnant or slow-flowing blood. This insufficiency will become more evident as a larger imaging volume is used, especially in 3-D imaging applications. Accordingly, it would be desirable to develop a better technique for black-blood imaging that is usable in 3-D applications.

To achieve sufficient blood suppression, flow-dephasing BB imaging techniques, such as a motion-sensitization driven equilibrium (MSDE) sequence, have recently been used for carotid artery vessel wall imaging. The MSDE technique utilizes a pair of flow sensitizing gradients to achieve BB imaging. The flow sensitizing gradient pair can introduce phase dispersion among moving spins, while maintaining the phase coherence of stationary spins. As has previously been reported, the flow suppression capability of the MSDE sequence is determined by the first-order moments ($m_1$) of the flow sensitizing gradient pair. Therefore, unlike IS and DIR techniques, the MSDE technique can theoretically eliminate any slow flowing blood artifact, as long as the first order moments $m_1$ of the gradient pair are strong enough.

One of the practical limitations of the MSDE technique is the inevitable signal loss that is caused by both the inherent $T_2$ decay and local magnetic field ($B_0$, $B_1$) inhomogeneity. Specifically (based on empirical experience), marked signal loss could be observed if the $m_1$ of the sequence is set to be large. This signal loss cannot be solely explained by an increased $T_2$ decay. Instead, it is likely that MSDE's sensitivity to the local $B_1$ inhomogeneity may play a key role in causing the signal loss. Therefore, a new scheme that is less sensitive to the $B_1$ inhomogeneity would clearly be desirable.

SUMMARY

To address the concerns noted above, the original MSDE pulse pattern that is used as a preparation sequence for other procedures employed to acquire images has been modified to produce an improved MSDE (iMSDE) sequence, by the addition of a second 180 degree refocusing pulse and two motion sensitization gradients. The iMSDE sequence thus includes a group of four RF pulses, as well as additional magnetic gradient pulses that are not included in the conventional MSDE sequence.

If the total duration between the 90 degree pulse occurring at the start of the preparation sequence and the 90 degree pulse occurring at the end of the preparation sequence is defined as $TE_{prep}$, the (time) gaps between the pulses in the group taken in order are $TE_{prep}/4$, $TE_{prep}/2$, and $TE_{prep}/4$, respectively. Four motion sensitization gradients with alternative polarities are fit into the RF pulse setup used in the iMSDE sequence. The scheme for placing sensitization gradients, G(u), employed, is selected to maximize the first gradient moment ($m_1$) within the fixed $TE_{prep}$ interval. The first gradient moment is the parameter that controls the flow suppression capability of the preparation pulse sequence.

Simulations have been performed to confirm some of the benefits of the iMSDE technique for the preparation pulse sequence, compared to the conventional MSDE technique. Specifically, the simulations show that signal levels in the traditional MSDE sequence drop significantly when the $rB_1$ value drifts from ideal conditions, while in contrast, signal levels are very retained in the iMSDE sequence, even when conditions are not ideal. Experiments have further shown that the new iMSDE sequence considerably improves the immunity of the method to $B_1$ inhomogeneities, and therefore, may extend MSDE applications in high-field imaging. The novel iMSDE preparation pulse sequence has application for imaging atherosclerosis plaque in arteries, BB coronary vessel wall imaging, and other applications in which it is important to remove the effects of flowing blood, while retaining details of a lumen wall in the MR images being acquired after the iMSDE pulse sequence.

Compared to the other black-blood techniques, the iMSDE pulse sequence is more suitable for 3-D imaging applications. As noted above, traditional black-blood techniques achieve black-blood effects based on the blood replenishing rate within the volume being imaged, and as a result, insufficient blood suppression is observed in regions where the blood flow is stagnant or slow. This problem increases if a larger imaging volume is used, especially in 3-D imaging applications. However, the iMSDE pulse technique is not limited by the imaging volume, since the technique does not rely on flow replenishing rate to achieve black-blood suppression. As shown in the images acquired using iMSDE in FIGS. 7A-7C, the present novel technique provides consistent blood suppression in a 3-D imaging environment, and the resulting images can easily be reformatted for display at various orientations, so that the plaque (and an ulcer) is readily evident within the blood vessel.

This application specifically incorporates by reference the disclosures and drawings of each patent application identified above as a related application.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 3A:
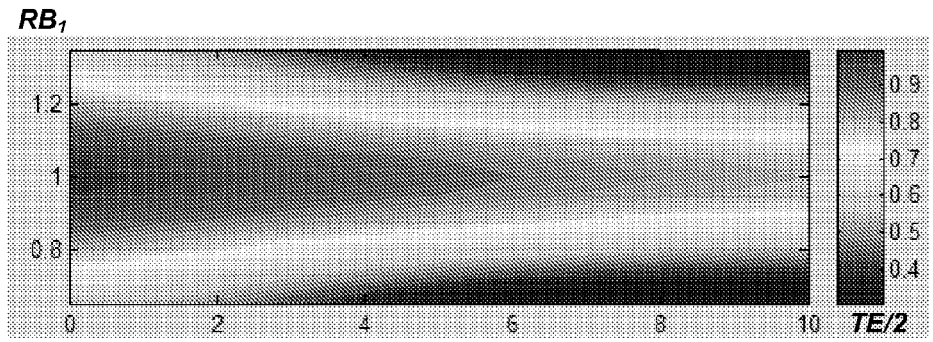
Figure 3B:
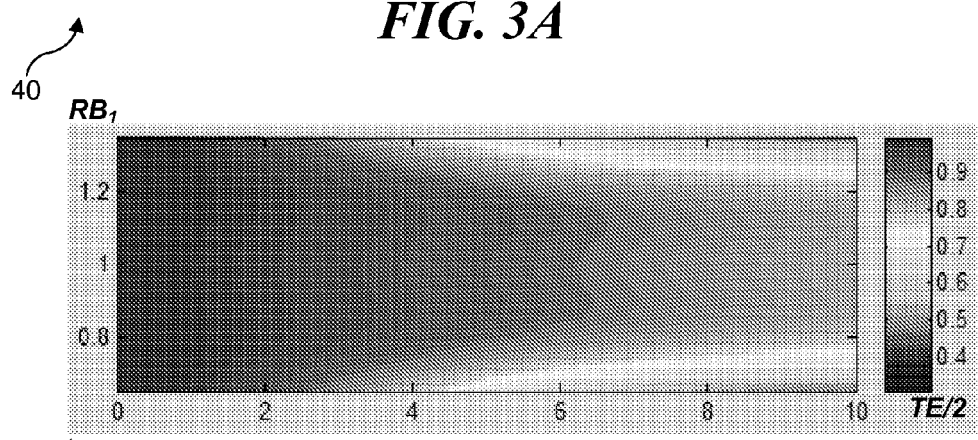
Figure 6:
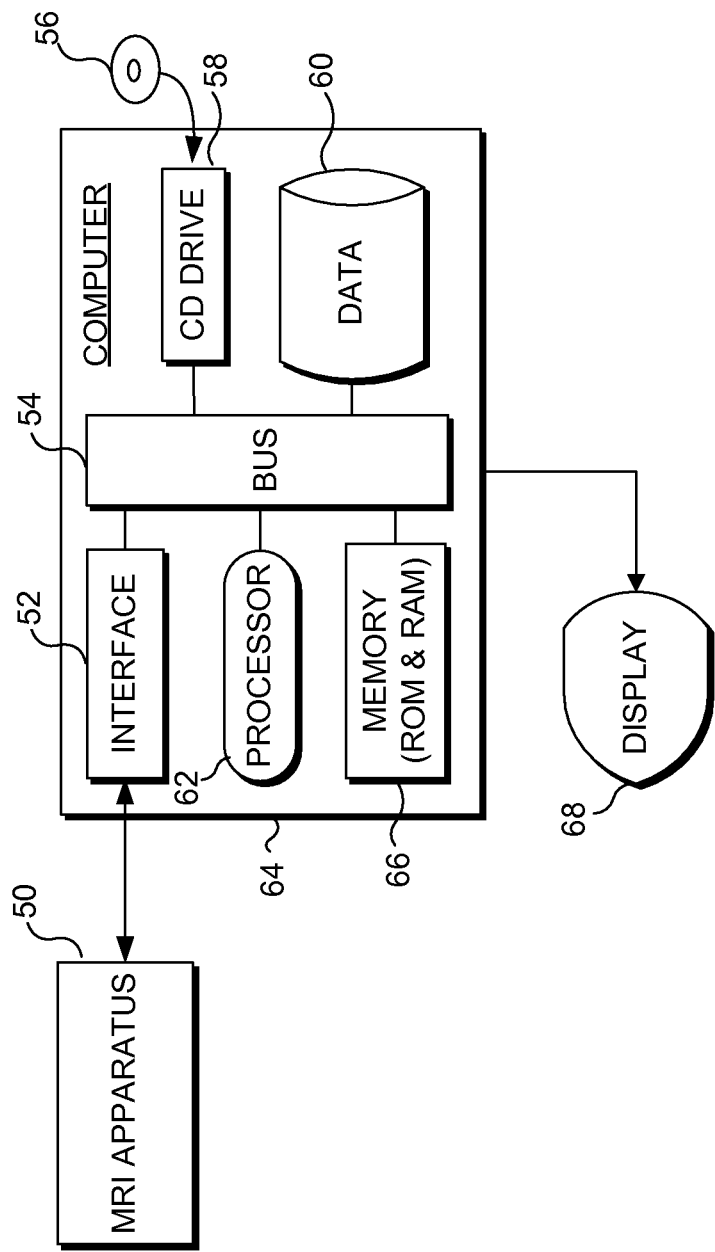
Figure 7A:
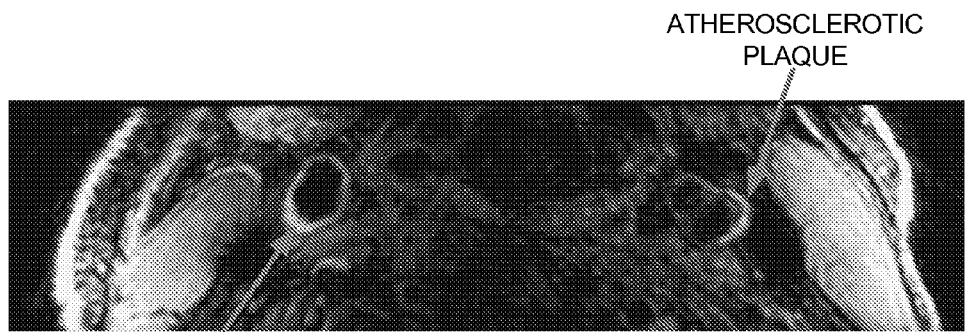
Figure 7B:
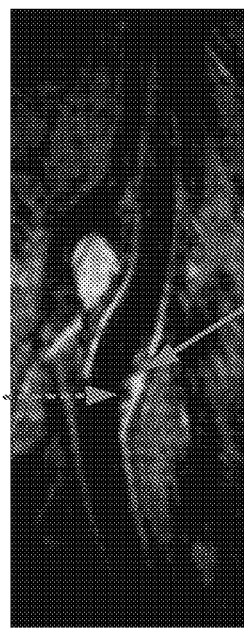
Figure 7C:

FIGS. 3A and 3B respectively illustrate simulation results used to estimate the signal level for MSDE and iMSDE sequences at different $rB_1$ and TE conditions, showing that the iMSDE sequence can generally provide higher signal levels than the conventional MSDE sequence;

FIGS. 4A and 4B respectively illustrate an exemplary MSDE image and a corresponding exemplary iMSDE image acquired when $m_1$ is set to a relatively high value (e.g., 1581 mTms$^2$/m in this case);

FIGS. 5A, 5B, and 5C respectively illustrate exemplary MSDE, iMSDE, and a $B_1$ map obtained from a phantom study;

FIGS. 5D-5F respectively illustrate exemplary signal profiles from the central lines in each of FIGS. 5A-5C;

FIGS. 5G and 5H respectively illustrate the measured and simulated signal ratio between iMSDE and MSDE images;

FIG. 6 is a block diagram illustrating an exemplary embodiment of a system used to implement the iMSDE technique; and FIGS. 7A, 7B, and 7C are respectively exemplary axial, sagittal, and coronal 3-D black-blood images, respectively, which were acquired using the present iMSDE pulse technique on a patient with atherosclerotic plaque, illustrating how sufficient blood flow suppression is achieved by the technique so that the plaque (solid arrows) and an ulcer (dotted arrow) is readily evident in the images.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

IMSDE Pulse Sequence

Figure 1A:
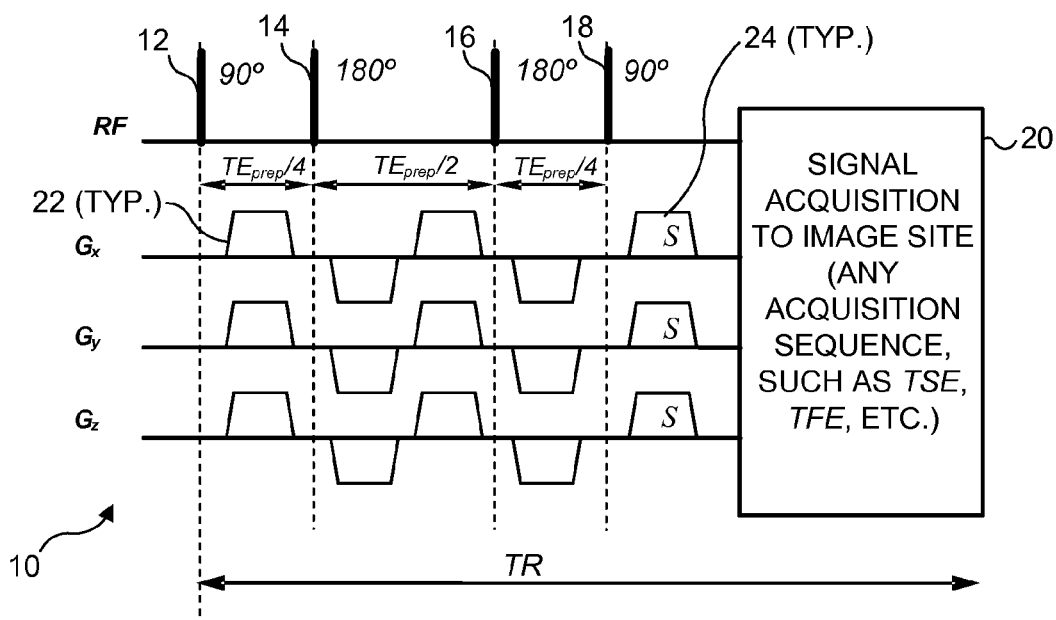
FIG. 1A is a graphic illustration showing an exemplary improved MSDE (iMSDE) pulse sequence scheme, wherein four radio frequency (RF) pulses are employed (trapezoids labeled S represent spoiling gradients, while open trapezoids represent motion sensitization gradients)

Compared to the traditional MSDE sequence, a major difference in an improved MSDE pulse sequence 10 that is discussed below is the addition of a second 180 degree refocusing pulse 16 (FIG. 1A).

A group of four radio frequency (RF) pulses 12, 14, 16, and 18 is constructed in the following way: if the total duration between 90° pulses 12 and 18 at opposite ends of the pulse sequence is defined as $TE_{prep}$, the gaps between RF pulses 12 and 14, 14 and 16, and 16 and 18 are $TE_{prep}/4$, $TE_{prep}/2$, and $TE_{prep}/4$, respectively.

To eliminate the phase coherence among moving spins, motion sensitization gradients need to be fit into this scheme. Accordingly, also shown in FIG. 1A are motion sensitization gradients $G_x$, $G_y$, and $G_z$ used in the iMSDE pulse sequence relative to the X, Y, and Z axes, respectively. Open trapezoids 22 represent these motion sensitization gradients, while trapezoids 24, which are labeled with an "S," represent spoiler gradients that are used to eliminate any residual magnetism. As noted above, the gradients should be constructed in the following way:

1. The zero$^{th}$ order gradient moment ($m_0$) should be zero, so that the phase coherence among stationary spins can be retained; and 2. The first order gradient moment ($m_1$) should be maximized for a given $TE_{prep}$, so that the phase coherence among flowing spins can be effectively eliminated.

Figure 1B:
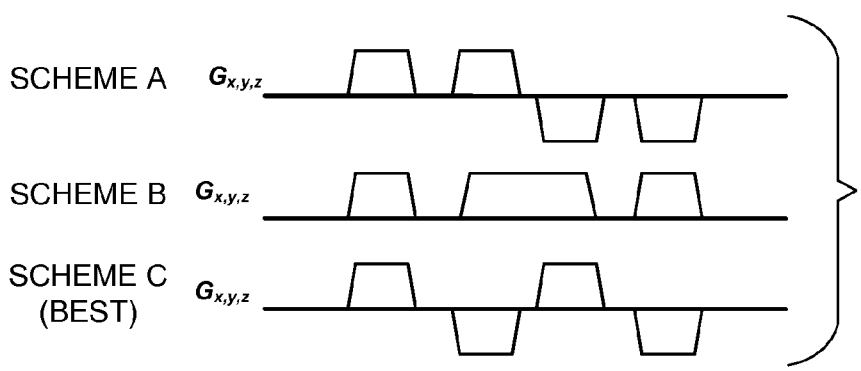
FIG. 1B illustrates three alternative motion sensitization magnetic field gradient schemes (A)-(C) that can be employed when performing iMSDE.

Considering only realistic gradient waveforms that might be used in the iMSDE sequence, there are three schemes (schemes <A>-<C> in FIG. 1B) that have zero $m_0$. All gradients presented in FIG. 1B used the maximum gradient strength and slew rates that are supported by the scanner hardware to achieve a greater $m_1$ for a fixed duration; all trapezoids have the same area except for the second trapezoid in scheme <B>, which is twice as long as the other trapezoids. The scheme with the highest first order gradient moment will be used for the scan. As indicated in a block 20, the sequence of RF pulses and gradients is followed by signal acquisition to image the site. Any of a number of different techniques can be applied to acquire the image following the iMSDE preparation sequence, as will be apparent to a person of ordinary skill in this technology.

The following equation is used to compute the first gradient moment of all three schemes:

$$m_1 = \int_0^T G(u)u\,du \quad (1)$$

where T is the total duration of all sensitization gradients, and G(u) is the magnetization gradient. Also, while calculating $m_1$, the 180° refocusing pulses are considered to have a net effect of inverting the polarity of all of the gradients that follow.

It is easy to prove that $m_{1c} > m_{1a} > m_{1b}$, if the gradient strength is not zero, i.e., scheme <C> has the greatest $m_1$ among all three schemes, which produces images with the greatest signal level. So scheme <C> is used as the optimal scheme for the iMSDE sequence.

Exemplary Flowchart for Producing Images Using iMSDE Sequence

Figure 2:
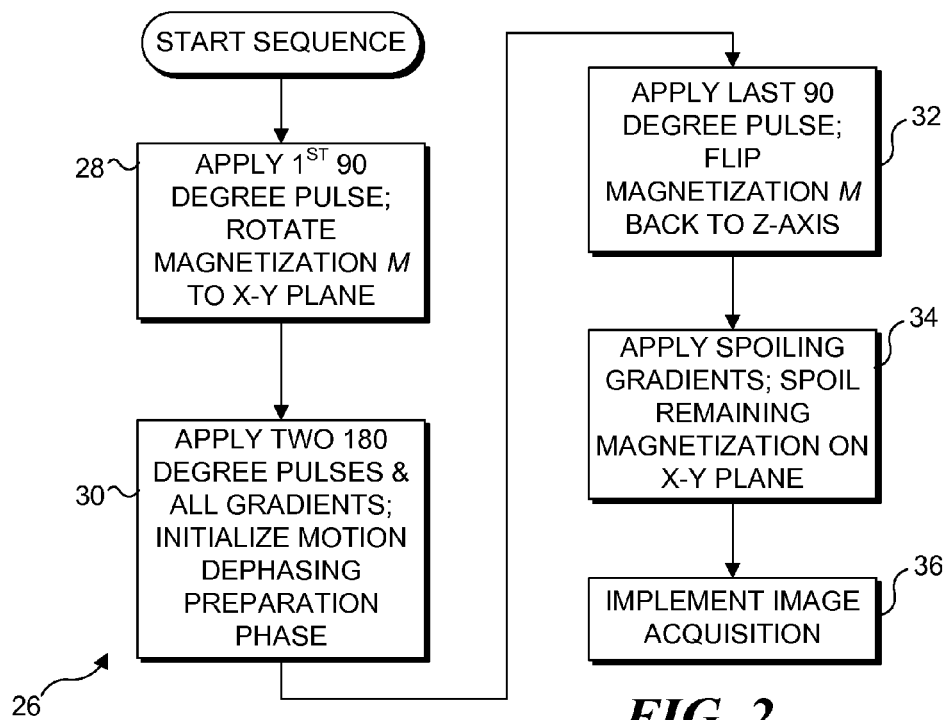
FIG. 2 is a flow chart illustrating exemplary steps for implementing the iMSDE preparation pulse sequence technique for imaging the walls of a vessel.

FIG. 2 illustrates exemplary logical steps for producing MRI images using the novel iMSDE preparation sequence described herein. After the start of the preparation sequence, a step 28 provides for rotating the magnetization, M, from the z-axis into the x-y plane, by applying a first 90 degree pulse. A step 30 provides for twice refocusing the applied signal in the motion dephasing preparation phase, by applying the two 180 degree pulses and all motion sensitization gradients. Next, a step 32 flips or rotates the magnetization, M, back to the z-axis, by applying a last 90 degree pulse. A step 34 spoils any remaining magnetization on the x-y plane, by using a spoiling gradient. Finally, image acquisition is implemented in a step 36. The specific details of the image acquisition sequence used for acquiring the image are not relevant to the preparation sequence, but it should be understood that a variety of different known techniques can be applied to acquire the image following the iMSDE preparation sequence.

Computer Simulations—Phantom and In Vivo

A Bloch equation-based computer program was used to evaluate the signal intensity of certain materials for different levels of $B_1$ inhomogeneity and $T_2$ decay. The simulation was conducted for both traditional and iMSDE sequences. All RF pulses were approximated as instantaneous, and the effect of gradients was not considered, since the simulation was not intended to estimate the flow suppression efficiency.

The computer simulation was designed to calculate the ratio of magnetizations, before and after the application of the prepulse, along the z-axis. Therefore, the closer the result achieved is to 1, the better the signal level will be retained after the prepulse. The computer simulations were realized through a custom-coded MATLAB™ program (available from Mathworks, Natick, Mass.).

Relative $B_1$ ($rB_1$) was used to simulate the $B_1$ inhomogeneity, and a single exponential $T_2$ decay was used to simulate the $T_2$ effect. The phantom simulation used values for $T_1$ and $T_2$ of 600 ms and 400 ms, respectively, to simulate a copper sulfate solution.

An in vivo simulation covered an $rB_1$ range of 0.65-1.35 and a $TE_{prep}$ range of 0-10 ms. Values used for $T_1$ and $T_2$ were 1000 ms and 200 ms, respectively.

Phantom Study

A phantom study was implemented to validate the hypothesis that $B_1$ inhomogeneity will cause a signal drop in a traditional MSDE image and to confirm that the improved MSDE sequence is less sensitive to the $B_1$ inhomogeneity.

The phantom that was used in this study is a round bottle filled with 2 g/L copper sulfate ($CuSO_4$ $5H_2O$) solution. MR images of the phantom were obtained on a 3 T clinical scanner (a Philips Achieva R2.1.1™, made in Best, Netherlands). A traditional MSDE image, an iMSDE image, and a $B_1$ map—all at the same spatial resolution, were acquired at the same locations.

The total durations for both MSDE and iMSDE prepulses were 19.4 and 21.2 ms, and all motion sensitization gradients were turned off in accordance with the simulation. Both sequences used the same PD-weighted TSE acquisition sequence, with the following parameters: TR/TE was 4000/8.5 ms, FOV was 160×120 mm, a matrix of 256×192 was used, the slice thickness was 2 mm, the echo train length was 12, the NSA was 1, 14 slices were imaged, and the total scan time was 2:16 (i.e., 2 minutes, 16 seconds).

Relative $B_1$ ($rB_1$) maps were acquired and calculated according to a previously proposed technique. The imaging parameters for the $B_1$ mapping sequences were as follows: $TR_1/TR_2/TE$ were 50/10/3.1 ms, respectively, the FOV was 160×120 mm, a matrix 256×192 mm was used, the slice thickness was 2 mm, the echo train length was 12, the NSA was 1, 14 slices were imaged, and the total scan time was 1:12 (i.e., one minute, 12 seconds).

Image Post-Processing

To better visualize the signal difference between MSDE and iMSDE images, a ratio map (Rmap) was calculated by computing the signal intensity ratio between the images on a pixel-by-pixel fashion, as described below:

$$I_{Rmap}(x,y) = I_{iMSDE}(x,y)/I_{MSDE}(x,y). \quad (2)$$

To validate the theoretical estimation, a simulated signal ratio map (SSRmap) was also calculated in a pixel-by-pixel fashion, based on the local $rB_1$ value, $T_1$, $T_2$, and $TE_{prep}$ of the sequence. The simulation was made by using the same simulation program noted above and as described below:

$$I_{SSRmap}(x,y) = B(rB_1(x,y), T_1(x,y), T_2(x,y), TE_{prep}). \quad (3)$$

The function B( ) indicates that the simulation is based on the Bloch equation. To simplify the simulation, the phantom is considered as homogeneous, and the same $T_1$ and $T_2$ values were used for all locations.

In Vivo Study Design and Population

Five healthy volunteers with no known cardiovascular disease (two male, three female, having a mean age of 56) were recruited in this study. Informed consent was obtained from all participants. The in vivo study was designed to compare the signal to noise ratio (SNR) level and flow suppression capability between traditional and iMSDE sequences for low, intermediate, and high $m_1$ situations.

MR Imaging

MR images of the carotid arteries were obtained on a 3 T (i.e., 3 Tesla) clinical scanner (a Philips Achieva R2.1.1™ made in Best, Netherlands) with a custom-designed four-channel phased-array bilateral carotid coil. The local Institutional Review Board has approved the coil for human research.

To compare the blood suppression efficiency of both the MSDE and iMSDE techniques, transverse images centered on the carotid bifurcation were obtained from all volunteers at identical anatomic locations, with both MSDE and iMSDE sequences. To assure a fair comparison, both techniques utilized the same gradient strength and same $m_1$. The detailed parameters are indicated in Table 2—below.

TABLE 2

Sequence Parameters for both MSDE and iMSDE Sequences

| | | Gradient Strength (mT/m) | Gradient Duration (ms) | Slew rate (mT/m/ms) | Total duration (ms) |
|---|---|---|---|---|---|
| High $m_1$ (1581 $mTms^2/m$) | MSDE | 20 | 7.5 | 100 | 19.4 |
| | iMSDE | 20 | 3.56 | 100 | 21.2 |

The parameters of both sequences were adjusted so that both sequences have the same $m_1$. All sequences used the same PD-weighted TSE acquisition sequence: the TR/TE was 4000/8.5 ms, the FOV was 160×120 mm, the matrix 256×192, the slice thickness was 2 mm, the echo train length was 12, the NSA was 1, 14 slices were imaged, and the total scan time was 2:16 (i.e., two minutes, 16 seconds).

Image Analysis

In the in vivo comparison study, the SNR in the carotid artery lumen was used as a measure of flow suppression efficiency, and the SNR of the sternocleidomastoid (SM) muscle was used as a measure of the overall signal intensity of each sequence. Images acquired at the same location with different sequences were manually registered using custom image analysis software, CASCADE. SNR measurements were performed in regions of interest (ROI), which were manually delineated on the lumen-wall boundary and the reference SM muscle on MSDE images. Contours were then automatically propagated to registered iMSDE images. The standard deviation (SD) of noise was measured from areas free from the signal and artifacts. The SNR for the lumen and SM were calculated as:

$$SNR = 0.695 \frac{S}{\sigma} \quad (4)$$

where S is the signal intensity, $\sigma$ is the SD of noise, and the multiplier 0.695 corresponds to a four-channel coil correction. Signal intensity and SD were automatically measured by CASCADE after the contours were drawn.

Statistical Analysis

Analysis was performed on the central six images covering the carotid bifurcation for each artery, because more distal artery segments are typically not prone to plaque-mimicking artifacts. For each subject, bilateral arteries were included in the analysis. Eight out of the total 60 locations were excluded because of the image quality decrease, which is primarily caused by the combination of both the severe signal loss of high $m_1$ MSDE images and reduced coil sensitivity for peripheral locations. For locations beyond the carotid artery bifurcation, internal carotid lumen SNR was recorded as a measure of flow suppression efficiency.

Statistical analysis was performed using Microsoft Corporation's Excel™ spreadsheet program. Two tailed paired Student's t-tests were conducted for both lumen and SM muscle SNR comparison in all groups. In all tests, statistical significance was defined at the p<0.05 level.

Results

Computer Simulations

Computer simulations 40 and 42 of signal intensity at different conditions are shown in FIGS. 3A and 3B, respectively. The color bar on the right side of each Figure indicates the residual magnetization after the MSDE/iMSDE preparation module was applied. The higher the value of magnetization that is applied, the higher is the signal level retained as the residual magnetization. The iMSDE sequence generally retains a higher residual signal level than the MSDE sequence at all conditions, with different TE and $rB_1$ combinations. The signal levels from the MSDE sequence always drop significantly when the $rB_1$ drifts from the ideal condition; while for the iMSDE sequence, signals are well retained at the same condition.

Phantom Study

The MSDE image, iMSDE image, and $B_1$ map of the same location are shown in FIGS. 5A-5C, respectively. Compared to the MSDE image in FIG. 5A, the iMSDE image in FIG. 5B presents a higher and more homogenous signal level (arrow), especially at the central and peripheral parts of the phantom, where $rB_1$ values are not ideal.

Situations can be better visualized if the signal profile of the center line is compared, as shown in FIGS. 5D-5F. As predicted in the simulation, when the $rB_1$ value drifts from 1, the signal intensities on the MSDE image drops quickly, and the signal intensities on the iMSDE image are relatively stronger and more robust to the $B_1$ variation (indicated at the arrow heads in FIGS. 5D and 5F).

The signal profile from the calculated Rmap, which shows the measured signal ratio between the iMSDE and MSDE images, and the simulated signal ratio map (SSRmap), which shows the simulated signal ratio between the iMSDE and MSDE images, are shown in FIGS. 5G and 5H. It is clear that measured signal ratio profile corresponds with the simulated signal ratio profile very well. This result also validates the hypothesis that $B_1$ inhomogeneity is the key to signal drop in MSDE images, while the signal drop is much reduced in iMSDE images.

In Vivo Comparison

For all images acquired at the same location, the iMSDE image always presents higher signal intensity compared to its MSDE counterpart at the same $m_1$ level. An example of this advantage is shown by the comparison between an MSDE image 46 in FIG. 4A and a corresponding iMSDE image 48 in FIG. 4B.

Comparisons of SNR for MSDE and iMSDE scans of a sternocleidomastoid muscle (SM) demonstrated a significantly higher SNR for the iMSDE technique (11.4±4.7 vs. 16.7±7.7, p<0.001).

Also, like the visual observation results, only slight lumen SNR differences were identified between MSDE and iMSDE images. The iMSDE image has a slight but significantly lower SNR (3.1±1.0, 2.7±0.9, p=0.001) when compared to that of the MSDE image.

Discussion

A flow dephasing-based MSDE BB sequence can achieve better slow flow suppression in carotid artery imaging compared to IS and DIR techniques. One limitation of the technique, however, is the signal loss caused by the $T_2$ decay and local $B_1$ inhomogeneity. This situation deteriorates very rapidly as stronger and longer motion sensitization gradients are used (thus, higher $m_1$) to suppress extremely slow and stagnant flow signal. The reason for the signal loss can at least partly be attributed to the high sensitivity of the MSDE sequence to the $B_1$ inhomogeneity.

The iMSDE technique that is disclosed herein effectively removes the $B_1$ sensitivity by employing an extra 180 degree refocusing pulse. As demonstrated in the results, the iMSDE sequence provides a significantly higher SNR. It is noteworthy that the signal improvement was achieved at almost no cost, i.e., the iMSDE sequence had the same flow suppression efficiency and same time efficiency as the MSDE sequence. The only potential downside is the need to apply an additional refocusing 180° pulse, which may make the sequence reach specific absorption rate (SAR) limits faster. But, at the 3 T environment used in this novel approach, the refocusing pulse did not limit the time efficiency of the iMSDE sequence.

Instead of using conventional RF pulses, the iMSDE sequence can also be constructed using adiabatic pulses, which are even less sensitive to the $B_1$ field inhomogeneity. However, using adiabatic pulses will significantly increase the duration of all RF pulses, leading to a much prolonged $TE_{prep}$ time.

Other than $B_1$ inhomogeneity, the $B_0$ field inhomogeneity could also be another limiting factor that leads to the signal drop in MSDE images. However, this effect is not considered in the present simulation, because the actual $B_0$ shift that was measured in vivo was merely 60 Hz for the carotid imaging setup.

As indicated by the results discussed above, the flow suppression efficiency of both the MSDE and iMSDE techniques improved along with the increase of motion sensitization gradient $m_1$. The flow artifact levels are also comparable between the MSDE and iMSDE images acquired under the same $m_1$ conditions. These observations are all in good agreement with the theoretical analysis that the first gradient moment ($m_1$) is a good measure of the flow suppression capability of the flow dephasing-based BB technique.

Another potential improvement provided as a benefit of using the iMSDE sequence is a lower sensitivity to eddy current effects. As discussed above, the iMSDE sequence setup is much less sensitive to the eddy current effect, which can potentially reduce the signal drop caused by the eddy current effect.

Although the flow suppression capability of the iMSDE sequence improved along with an $m_1$ increase, the overall carotid artery composite noise ratio (CNR) decreased. Here, CNR was defined as the SNR difference between the SM muscle and CA lumen. Generally, a CNR decrease indicates a less preferable situation for image review. In vessel wall imaging, however, a solely decreased CNR may not always indicate a bad thing. It should be evaluated in combination with the flow artifact elimination effectiveness. A good application for the iMSDE imaging, therefore, is as a lumen/wall boundary identification sequence in a carotid artery imaging protocol. In this way, the lumen/wall boundary can be reliably identified through the high $m_1$ iMSDE sequence and the tissue components can be identified through other imaging sequences.

Some other potential applications of the iMSDE pulse sequence include the peripheral artery imaging and high field imaging applications. In peripheral artery imaging, the flow velocity is much lower than that in the major arteries such as the carotid artery. Therefore, a sequence with both high blood flow suppression capability and good signal level, such as iMSDE sequence, is desired. For high field imaging applications, the increased field strength may become a more stringent environment to achieve a homogeneous $B_1$ field. In this situation, the traditional MSDE sequence may present even higher signal loss because of the worsened $B_1$ field. So, the iMSDE sequence, which is less sensitive to $B_1$ variation, may become a more practical solution for addressing that problem.

Optimization of iMSDE Sequence for Different Vascular Beds

Since the iMSDE sequence suppresses the blood signal based on the spin dephasing effect, the blood suppression efficiency will be affected by the local flow distribution and other factors such as spatial resolution and slice thickness. To achieve a balance between the optimized flow suppression and general image quality for a particular imaging application, the imaging parameters should be empirically optimized.

Since the first gradient moment ($m_1$) of the iMSDE sequence governs the flow suppression, it will be important to optimize the $m_1$ values of the sequence. The $m_1$ values are defined overall by the gradient strength and duration. The gradient duration determines the total preparation time ($TE_{prep}$). Since the longer the $TE_{prep}$, the stronger the $T_2$ decay effect, the optimization should always start from the strongest gradient strength available on the MRI scanner in an effort to shorten the $TE_{prep}$.

After the targeted imaging plane is identified for the imaging subject, a series of MR images should be planned at the same imaging locations with different gradient durations, in an effort to optimize the black-blood imaging efficiency by selecting the duration that produces the best results. The gradient durations attempted should cover a relatively broad range to ensure that optimized parameters will be identified through this experiment. For example, for a carotid artery imaging application, a set of durations might be in integer ms increments: 0, 1, 2, 3, 4, . . . 10 ms.

In cases when image artifacts can be observed at maximum gradient strength (for example, due to eddy currents), the gradient strength used in the study will need to be gradually reduced until a satisfactory image quality is achieved. It may then be necessary to repeat the empirical procedures described above, in the preceding paragraph.

After all the MR images are acquired at different gradient durations, the black-blood image quality can be evaluated by the wall/lumen CNR. Generally, the CNR will increase, as the gradient duration increases in the first portion of the empirical gradient intervals, due to improved blood suppression and then decrease, as the duration continues to increase, due to the signal loss in the vessel wall. The parameters corresponding to the maximized CNR can thus be identified as the optimized imaging parameter for the iMSDE sequence for that particular application and should be used in the future scans for corresponding applications.

Exemplary System for Implementing iMSDE Technique

FIG. 6 schematically illustrates an exemplary system suitable for implementing the iMSDE technique. The system includes a generally conventional magnetic resonance imaging (MRI) apparatus 50 that is controlled by a computer 64. Computer 64 may be a generally conventional personal computer (PC) or a dedicated controller specifically intended for controlling MRI apparatus 50. Although not shown, MRI apparatus 50 includes a magnet to create a permanent magnetic field, a plurality of gradient coils to produce spatial variations of magnetic field, and RF transceiver and receiver systems to transmit and receive RF signals to and from a plurality of RF coils, as will be well known to those of ordinary skill in the art of MRI. Accordingly, details of the MRI apparatus need not be and are not specifically illustrated or discussed herein.

Computer 64 is coupled to a display 68, which is used for displaying MRI images of image slices to an operator. Included within computer 64 is a processor 62. A memory 66 (with both read only memory (ROM) and random access memory (RAM)), a non-volatile storage 60 (such as a hard drive or other non-volatile data storage device) for storage of data, digital signals, and software programs, an interface 52, and an optical drive 58 are coupled to processor 62 through a bus 54. Optical drive 58 can read a compact disk (CD) 56 (or other optical storage media, such as a digital video disk (DVD)) on which machine instructions are stored for implementing the present novel technique, as well as other software modules and programs that may be run by computer 64. The machine instructions are loaded into memory 66 before being executed by processor 62 to carry out the steps for implementing the iMSDE technique.

Operation of MRI apparatus 50 is controlled by computer 64 when processor 62 executes the machine instructions stored in memory 66. These machine instructions cause the processor to control the MRI apparatus so that it applies the pulse sequences to a biological entity and acquires the resulting signals that are output from the MRI apparatus. The resulting signals are optionally stored on storage 60 so that selected images can subsequently be displayed on display 68, or can instead be directly displayed as the output signals are acquired. It is also noted that the machine instructions can cause processor 62 to determine the appropriate predefined variables, so as to ensure that the biological entity is appropriately imaged in accord with the iMSDE technique.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method, comprising:
   (a) using a magnetic resonance imaging (MRI) device, administering a preparation sequence configured to suppress a contribution due to flowing blood in an MRI signal of a site in a subject, the administering of the preparation sequence including:
      (i) applying four radio frequency (RF) pulses to the site at predefined time intervals;
      (ii) applying a plurality of motion sensitizing magnetic field gradients to the site, for each of a plurality of orthogonal axes, wherein the motion sensitizing magnetic field gradients are applied between the RF pulses; and
      (iii) applying a spoiler magnetic field gradient to the site after a last of the four RF pulses; and
   (b) after the administering of the preparation sequence and using the MRI device, performing an image acquisition sequence to acquire a magnetic resonance image signal that is usable to image the site, the preparation sequence reducing contributions to the magnetic resonance image signal from flowing blood at the site;
   wherein applying the plurality of motion sensitizing magnetic field gradients further comprises constructing the plurality of motion sensitizing magnetic field gradients so that a phase coherence among stationary spins at the site is retained.

2. The method of claim 1, wherein the step of applying the four RF pulses includes the step of applying, in order:
   (a) a first 90 degree RF pulse;
   (b) a first 180 degree RF pulse;
   (c) a second 180 degree RF pulse; and
   (d) a second 90 degree pulse.

3. The method of claim 2, wherein the step of applying the four RF pulses comprises the step of applying the four RF pulses to the site over a predefined preparation period, $TE_{prep}$, using predefined time intervals between the first 90 degree RF pulse and the first 180 degree RF pulse, and between the second 180 degree RF pulse and the second 90 degree pulse that are equal to $TE_{prep}/4$, and using a predefined time interval between the first 180 degree RF pulse and the second 180 degree RF pulse that is equal to $TE_{prep}/2$.

4. The method of claim 3, wherein for the plurality of motion sensitizing magnetic field gradients are configured to increase a first order gradient moment.

5. The method of claim 1, wherein the step of applying the four RF pulses comprises the steps, in order, of:
   (a) rotating a magnetization at the site from a selected one of the orthogonal axes, into a plane defined by two others of the orthogonal axes;
   (b) providing a first refocus of the signal at the site;
   (c) providing a second refocus of the signal at the site; and
   (d) rotating the magnetization from the plane back into alignment with the selected one of the orthogonal axes.

6. The method of claim 1, wherein for each of the plurality of orthogonal axes, the step of applying the plurality of motion sensitizing magnetic field gradients includes the steps of:
   (a) applying a first motion sensitizing magnetic field gradient during a first predefined time interval between a first and a second of the RF pulses;
   (b) applying at least one motion sensitizing magnetic field gradient during a second predefined time interval between the second and a third of the RF pulses; and
   (c) applying a final motion sensitizing magnetic field gradient during a third predefined time interval between the third and a fourth of the RF pulses.

7. The method of claim 1, wherein for each of the plurality of orthogonal axes, the step of applying the plurality of motion sensitizing magnetic field gradients includes the step of applying four alternating polarity motion sensitizing magnetic field gradients, with one of the four motion sensitizing magnetic field gradients being applied during a first predefined time interval between a first and second of the RF pulses, two of the motion sensitizing magnetic field gradients being applied during a second predefined time interval between the second and a third of the RF pulses, and one of the four motion sensitizing magnetic field gradients being applied during a third predefined interval between the third and a fourth of the RF pulses.

8. The method of claim 1, wherein the step of applying the plurality of motion sensitizing magnetic field gradients is configured to suppress phase coherence among spins in the moving blood.

9. A non-transitory storage medium storing instructions readable and executable by a computing device to cause the computing device to:
   (a) control a magnetic resonance imaging (MRI) device to administer a blood suppression preparatory sequence to a site in a subject, wherein the blood suppression preparatory sequence comprises:
      (i) four radio frequency (RF) pulses applied to the site at predefined time intervals;
      (ii) a plurality of motion sensitizing magnetic field gradients applied to the site, for each of a plurality of orthogonal axes; and
      (iii) a spoiler magnetic field gradient applied to the site after a last of the four RF pulses; and
   (b) control the MRI device to implement an image acquisition sequence after completion of the blood suppression preparatory sequence to acquire a magnetic resonance image signal that is usable to image the site;
   wherein the plurality of motion sensitizing magnetic field gradients are configured to be applied so that a phase coherence among stationary spins at the site is retained.

10. An apparatus, comprising:
    a memory in which are stored machine readable instructions; and
    a processor that is operatively coupled to the memory and to a magnetic resonance imaging device, the processor configured to read and execute the machine readable instructions stored in the memory to perform operations including:
    (i) controlling a magnetic resonance imaging (MRI) device to administer a preparatory sequence comprising:
       (1) four radio frequency (RF) pulses applied to the site at predefined time intervals;

(2) a plurality of motion sensitizing magnetic field gradients applied to the site, for each of a plurality of orthogonal axes; and (3) a spoiler magnetic field gradient applied to the site after a last of the four RF pulses; and (ii) controlling the MRI device, to perform an image acquisition sequence to acquire a magnetic resonance image of the site with contribution to the magnetic resonance image from flowing blood at the site reduced by the administered preparatory sequence;

wherein the plurality of motion sensitizing magnetic field gradients are configured so that a phase coherence among stationary spins at the site is retained.

11. The apparatus of claim 10, wherein the four RF pulses of the preparatory sequence are, in order:

(a) a first 90 degree RF pulse;

(b) a first 180 degree RF pulse;

(c) a second 180 degree RF pulse; and (d) a second 90 degree pulse.

12. The apparatus of claim 11, wherein the four RF pulses are applied to the site over a predefined preparation period, $TE_{prep}$, using predefined time intervals between the first 90 degree RF pulse and the first 180 degree RF pulse, and between the second 180 degree RF pulse and the second 90 degree pulse that are equal to $TE_{prep}/4$, and using a predefined time interval between the first 180 degree RF pulse and the second 180 degree RF pulse that is equal to $TE_{prep}/2$.

13. The apparatus of claim 12, wherein the plurality of motion sensitizing magnetic field gradients are configured to increase a first order gradient moment so as to suppress phase coherence among spins in the flowing blood.

14. The apparatus of claim 10, wherein the four RF pulses applied to the site are configured to:

(a) rotate a magnetization at the site from a selected one of the orthogonal axes into a plane defined by two others of the orthogonal axes;

(b) provide a first refocus of the signal at the site;

(c) provide a second refocus of the signal at the site; and (d) rotate the magnetization from the plane back into alignment with the selected one of the orthogonal axes.

15. The apparatus of claim 10, wherein the plurality of motion sensitizing magnetic field gradients include, for each of the plurality of orthogonal axes:

(a) a first motion sensitizing magnetic field gradient applied during a first predefined time interval between a first and a second of the RF pulses;

(b) at least one motion sensitizing magnetic field gradient applied during a second predefined time interval between the second and a third of the RF pulses; and (c) a final motion sensitizing magnetic field gradient applied during a third predefined time interval between the third and a fourth of the RF pulses.

16. The apparatus of claim 10, wherein for each of the plurality of orthogonal axes, the plurality of motion sensitizing magnetic field gradients include four alternating polarity motion sensitizing magnetic field gradients, with one of the four motion sensitizing magnetic field gradients being applied during a first predefined time interval between a first and second of the RF pulses, two of the motion sensitizing magnetic field gradients being applied during a second predefined time interval between the second and a third of the RF pulses, and one of the four motion sensitizing magnetic field gradients being applied during a third predefined interval between the third and a fourth of the RF pulses.

17. The apparatus of claim 10, wherein the plurality of motion sensitizing magnetic field gradients are configured to suppress phase coherence among spins in the moving blood while not suppressing phase coherence among stationary spins.

18. A method comprising:

(a) using a magnetic resonance imaging (MRI) device, applying to a site a sequence of radio frequency (RF) pulses and magnetic field gradients that includes, in order:

(i) a first 90 degree RF pulse;

(ii) a first motion sensitizing magnetic field gradient at a first polarity;

(iii) a first 180 degree RF pulse;

(iv) a second motion sensitizing magnetic field gradient at a second polarity that is opposite the first polarity;

(v) a third motion sensitizing magnetic field gradient at the first polarity;

(vi) a second 180 degree RF pulse;

(vii) a fourth motion sensitizing magnetic field gradient at the second polarity;

(viii) a second 90 degree RF pulse; and (ix) a spoiler magnetic field gradient, wherein the each of the motion sensitizing magnetic field gradients and the spoiler gradient are applied on each of a plurality of orthogonal axes; and (b) using the MRI device, performing an image acquisition sequence to acquire a magnetic resonance image of the site;

wherein operations (a)(ii), (a)(iv), (a)(v), and (a)(vii) are configured to retain phase coherence among stationary spins at the site.

19. The method of claim 18, wherein the operation (a) employs a time interval between the first and the second 180 degree RF pulse that is about twice a time interval between the first 90 degree RF pulse and the first 180 degree RF pulse, and about twice a time interval between the second 180 degree RF pulse and the second 90 degree RF pulse.

20. The method of claim 18, wherein operation (a) is configured to reduce $B_1$ inhomogeneity sensitivity.

21. The method of claim 18, wherein operations (a)(ii), (a)(iv), (a)(v), and (a)(vii) are configured to retain phase coherence among stationary spins at the site while suppressing phase coherence among spins in the moving blood.

22. The method of claim 18, wherein operations (a)(ii), (a)(iv), (a)(v), and (a)(vii) are configured to increase a first order gradient moment for each of the orthogonal axes, so that a phase coherence among spins in flowing blood is reduced.

23. The method of claim 18, wherein the operations (a)(ii), (a)(iv), (a)(v), and (a)(vii) are configured to reduce a contribution to the magnetic resonance image signal due to flowing blood.

24. The method of claim 1, wherein the four RF pulses include a plurality of 180 degree refocusing RF pulses; and wherein a zero$^{th}$ order gradient moment ($m_0$) of the plurality of motion sensitizing magnetic field gradients is zero and a first order gradient moment ($m_1$) of the plurality of motion sensitizing magnetic field gradients is nonzero.

25. The non-transitory storage medium of claim 9, wherein the four RF pulses are applied over a preparatory time interval $TE_{prep}$, the four RF pulses including a plurality of 180 degree refocusing pulses; and wherein the plurality of motion sensitizing magnetic field gradients are applied to the site over the preparatory time interval $TE_{prep}$.

26. The apparatus of claim 10, wherein a zero$^{th}$ order gradient moment ($m_0$) of the plurality of motion sensitizing magnetic field gradients is zero and a first order gradient moment ($m_1$) of the plurality of motion sensitizing magnetic field gradients is nonzero.

27. The method of claim 1, wherein the four RF pulses comprise an MLEV-4 pulse scheme.

28. The method of claim 1, wherein the applied plurality of motion sensitizing magnetic field gradients have a first duration; and wherein the method further comprises imaging the site a second time by repeating steps (a)-(b) and using a plurality of motion sensitizing magnetic field gradients having a second duration different from the first duration.

29. The method of claim 1, wherein the site is imaged a plurality of times by repeating steps (a)-(b) a plurality of times, wherein each repetition of steps (a)-(b) applies a different duration for the plurality of motion sensitizing magnetic field gradients for each of the plurality of times.

30. The method of claim 29, wherein the different durations for the plurality of motion sensitizing magnetic field gradients are in a range between 0-10 ms.

31. The method of claim 29, further comprising identifying an optimized duration of the applied plurality of motion sensitizing magnetic field gradients based on a wall/lumen contrast-to-noise ratio.

32. The method of claim 31, wherein the optimized duration of the applied plurality of motion sensitizing magnetic field gradients is associated with the greatest wall/lumen contrast-to-noise ratio out of the wall/lumen contrast-to-noise ratios associated with the plurality of motion sensitizing magnetic field gradients of different durations.

33. The method of claim 1, further comprising:
   acquiring a first image from the magnetic resonance image signal;
   identifying image artifacts in the first image; and
   in response to identifying image artifacts in the first image, reducing a duration of the applied plurality of motion sensitizing magnetic field gradients and repeating steps (a)-(b) using the reduced duration of the plurality of motion sensitizing magnetic field gradients.

34. The method of claim 1, wherein the four applied RF pulses comprise adiabatic pulses.

* * * * *